(12) United States Patent
Fuchs et al.

(10) Patent No.: US 8,184,766 B2
(45) Date of Patent: May 22, 2012

(54) X-RAY COMPUTER TOMOGRAPH AND METHOD FOR INVESTIGATING AN OBJECT BY MEANS OF X-RAY COMPUTER TOMOGRAPHY

(75) Inventors: Theobald Fuchs, Nürnberg (DE); Norman Uhlmann, Erlangen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 23 days.

(21) Appl. No.: 12/918,403

(22) PCT Filed: Feb. 25, 2009

(86) PCT No.: PCT/EP2009/001325
§ 371 (c)(1),
(2), (4) Date: Aug. 19, 2010

(87) PCT Pub. No.: WO2009/106304
PCT Pub. Date: Sep. 3, 2009

(65) Prior Publication Data
US 2010/0316183 A1  Dec. 16, 2010

(30) Foreign Application Priority Data
Feb. 27, 2008 (DE) .......................... 10 2008 011 391

(51) Int. Cl.
*A61B 6/00* (2006.01)

(52) U.S. Cl. .............................................. 378/6; 378/7

(58) Field of Classification Search .................... 378/6, 7
See application file for complete search history.

(56) References Cited

U.S. PATENT DOCUMENTS

| | | | |
|---|---|---|---|
| 6,134,297 A | 10/2000 | Chao | |
| 6,256,367 B1 | 7/2001 | Vartanian | |
| 6,636,622 B2 * | 10/2003 | Mackie et al. | 382/132 |
| 6,687,326 B1 | 2/2004 | Bechwati et al. | |
| 6,925,140 B2 | 8/2005 | Bruder | |
| 7,627,079 B2 * | 12/2009 | Boone | 378/4 |
| 7,711,090 B2 * | 5/2010 | Schweizer et al. | 378/98.12 |
| 8,000,512 B2 * | 8/2011 | Sabol et al. | 382/132 |
| 2003/0210761 A1 | 11/2003 | Hoffman | |
| 2004/0091079 A1 | 5/2004 | Zapalac | |

FOREIGN PATENT DOCUMENTS

| | | |
|---|---|---|
| DE | 102005043050 | 3/2007 |
| EP | 1 192 900 | 4/2002 |
| EP | 1 553 407 A1 | 7/2005 |
| EP | WO 2006/056915 | 6/2006 |

OTHER PUBLICATIONS

M. Bertram et al.; Potential of software-based scatter corrections in cone-beam volume CT; Medical Imaging 2005: Physics of Medical Imaging, edited by Michael J. Flynn; Proceedings of SPIE vol. 5745; pp. 259-269.

* cited by examiner

*Primary Examiner* — Alexander H Taningco
(74) *Attorney, Agent, or Firm* — McGlew and Tuttle, P.C.

(57) ABSTRACT

In an X-ray computer tomograph and a method for investigating an object by means of X-ray computer tomography, to improve the image quality, a first intensity of the X-ray radiation between an X-ray source and the object is measured by means of a first intensity measurement device (13) and a second intensity of the X-ray radiation between the object and the X-ray detector outside a projection region of the object is measured by means of a second intensity measurement device. A scattered radiation correction factor is calculable by means of the measured intensities to reduce the scattered radiation.

19 Claims, 3 Drawing Sheets

X-RAY COMPUTER TOMOGRAPH AND METHOD FOR INVESTIGATING AN OBJECT BY MEANS OF X-RAY COMPUTER TOMOGRAPHY

CROSS REFERENCE TO RELATED APPLICATIONS

This application is a United States National Phase application of International Application PCT/2009/001325 and claims the benefit of priority under 35 U.S.C. §119 of German patent application DE 10 2008 011 391.3 filed Feb. 28, 2008, the entire contents of which are incorporated herein by reference.

FIELD OF THE INVENTION

The invention relates to an X-ray computer tomograph for investigating an object by means of X-ray computer tomography comprising an X-ray source for generating X-ray radiation, an X-ray detector for detecting the X-ray radiation, an object carrier for positioning an object to be investigated between the X-ray source and the X-ray detector, and an evaluation unit for evaluating the detected X-ray radiation. The invention furthermore relates to a method for investigating an object by means of X-ray computer tomography comprising the steps of positioning an object to be investigated between an X-ray source and an X-ray detector, irradiating the object with X-ray radiation, detecting the X-ray radiation, and evaluating the detected X-ray radiation by means of an evaluation unit.

BACKGROUND OF THE INVENTION

X-ray computer tomography (CT) allows destruction-free and contactless investigation of the inner structure of an object. It is used both in the medical area for investigating the human body and also in the industrial area for quality checking. An important step in X-ray computer tomography is the standardization of the intensity of the X-ray radiation, which is measured behind the object to be investigated by means of an X-ray detector. This generally takes place in such a way that a grey-scale value is determined in the detector, which is interpreted as the reference value for the unattenuated primary X-ray radiation. Using this reference value, the grey-scale values resulting from the X-ray radiation attenuated by the object are standardized.

When using integrating, non-energy-dissipating X-ray detectors, as is conventional in destruction-free checking of objects in the industrial area, there is no possibility for deciding whether the photons impinging on the X-ray detector are to be assigned to the primary X-ray radiation or the secondary X-ray radiation. The photons of the primary X-ray radiation arrived, without interacting in the object to be investigated with said object, from the X-ray source to the X-ray detector, whereas the photons of the secondary X-ray radiation were produced in a scattering process in the object. The measurement of the intensity attenuated by the object by means of the X-ray detector therefore also contains—in addition to the fluorescent radiation induced in the object—a contribution of the randomly scattered photons, in other words a contribution of the secondary X-ray radiation. The secondary X-ray radiation is also designated scattered radiation. The scattered radiation falsifies the measurement of the attenuated primary X-ray radiation, so the image quality of reconstructed images of the object is impaired.

SUMMARY OF THE INVENTION

The invention is therefore based on the object of providing an X-ray computer tomograph, which allows the recording of images of an object to be investigated with a high image quality.

This object is achieved according to the invention by an X-ray computer tomograph, in which a first intensity measurement device for measuring a first intensity of the X-ray radiation is arranged between the X-ray source and the object carrier, in which a second intensity measurement device for measuring a second intensity of the X-ray radiation is arranged between the object carrier and the X-ray detector outside a projection region of the object, in which the intensity measurement devices are connected to the evaluation unit to transmit the measured intensities, and in which the evaluation unit is configured in such a way that at least one scattered radiation correction factor is calculable depending on the measured intensities. According to the invention, it was recognized that, using two intensity measurements, a scattered radiation correction factor is calculable, by means of which the influence of the scattered radiation can be corrected. Using the first intensity measurement device, which is arranged between the X-ray source and the object carrier equipped with the object to be investigated, an intensity of the unattenuated primary X-ray radiation is measurable. Using the second intensity measurement device, which is arranged between the object carrier and the X-ray detector outside the projection region of the object to be investigated, an intensity can be measured, which is substantially composed of the intensity of the unattenuated primary X-ray radiation and the scattered radiation intensity, in other words the intensity of the secondary X-ray radiation. The scattered radiation correction factor, which characterizes the scattered radiation produced by the object, can be calculated from the measured intensities. The scattered radiation correction factor is a correction value, which, as a factor in the strictly mathematical sense or in another mathematical form, can be entered in a scattered radiation correction. Using this scattered radiation correction factor, assuming a scattered radiation distribution of zero or a higher order, a correction of the intensities measured by the X-ray detector can be carried out for each individual pixel. The influence of the scattered radiation can therefore be substantially eliminated, which leads to an improvement in the image quality of the X-ray computer tomograph. Moreover, the measurement of the intensity of the unattenuated primary X-ray radiation supplies a reliable standardization variable for standardizing the intensities measured by the X-ray detector. The image quality is also improved by this.

A development, in which a first spacing defined as the shortest axial distance of the first intensity measurement device from the X-ray source in relation to a second spacing defined as the shortest axial distance of the first intensity measurement device from the object carrier is smaller than ½, in particular smaller than ¼ and, in particular, smaller than ⅛, improves the accuracy of the measurement of the intensity of the unattenuated primary X-ray radiation. The closer to the X-ray source the first intensity measurement device is arranged, the higher the measuring accuracy.

By an arrangement of the first intensity measurement device, in which the first intensity measurement device is arranged outside an irradiation region of the object, the first intensity measurement device is prevented from being visible in a projection of the object to be investigated.

The precision of the measurement of the second intensity is improved by a development, in which a third spacing defined as the shortest axial distance of the second intensity device from the X-ray detector in relation to a fourth spacing defined as the shortest axial distance of the second intensity measurement device from the object carrier is smaller than ½, in particular smaller than ¼ and, in particular, smaller than ⅛. The closer to the X-ray detector the second intensity measurement device is arranged, the more precisely the influence of the scattered radiation can be measured and calculated.

A configuration of the intensity measurement devices as electronic dosimeters is economical.

A development, in which the intensity measurement devices are constructed identically, simplifies the calculation of the at least one scattered radiation correction factor. The signals of the intensity measurement devices may be directly further processed because of the structurally identical configuration, without a standardization of the signals to a uniform reference size having to be carried out. Structurally identical intensity measurement devices accordingly do not have to be calibrated.

A high image quality can be achieved by a development, in which the first intensity measurement device is arranged in such a way that an intensity of an unattenuated primary X-ray radiation is measurable as the first intensity and the second intensity measurement device is arranged in such a way that an intensity, which is composed of the intensity of the unattenuated primary X-ray radiation and an intensity of a secondary X-ray radiation, is measurable as the second intensity.

A development, in which the intensity measurement devices are arranged in a measurement region, in which a primary unattenuated X-ray radiation arrives from the X-ray source at the X-ray detector, without impinging on the object to be investigated, allows a precise measurement of the intensity of the unattenuated primary X-ray radiation by means of the first intensity measurement device and of the intensity composed of the intensity of the unattenuated primary X-ray radiation and the intensity of the secondary X-ray radiation, by means of the second intensity measurement device.

A development, in which the evaluation unit is configured in such a way that, for each pixel P of the X-ray detector, a corrected attenuation value is calculable according to the equation $$A(x, y) = -\ln\left[\frac{g(x, y)}{k \cdot I_0} + 1 - F\right]$$

wherein
A(x,y) is the corrected attenuation value for the pixel P(x,y),
g(x,y) is a measured grey-scale value for the pixel P(x,y),
$k \cdot I_0$ is a constant which is determinable in preliminary tests and
F is the scattered radiation correction factor,
allows corrected attenuation values to be calculated for each pixel of the X-ray detector, by means of which an X-ray image can be produced in the evaluation unit with the aid of known reconstruction algorithms. With a scattered radiation correction of zero order, the scattered radiation correction factor is produced as a quotient of the second intensity and the first intensity. With a scattered radiation correction of a higher order, the scattered radiation correction factor is produced as a product of this quotient and the associated Monte Carlo scattered radiation distribution.

The invention is also based on the object of providing a method for investigating an object by means of X-ray computer tomography, which allows a high image quality.

This object is achieved according to the invention by a method, in which, during the irradiation of the object, a first intensity of the X-ray radiation between the X-ray source and the object is measured, in which, during the irradiation of the object, a second intensity of the X-ray radiation between the object and the X-ray detector outside a projection region of the object is measured, and in which, during the evaluation, at least one scattered radiation correction factor is calculated depending on the measured intensities and the detected X-ray radiation is corrected with the at least one scattered radiation correction factor. The advantages of the method according to the invention correspond to the advantages already described of the X-ray computer tomograph according to the invention.

A development, in which the intensities are measured at the same time, ensures a time allocation of the measured values and therefore a reliable and accurate correction of the scattered radiation.

A measurement, in which the first intensity is measured outside an irradiation region of the object, prevents the first intensity measurement device being visible in projections of the object to be investigated.

A calculation of the at least one scattered radiation correction factor, in which at least one Monte Carlo scattered radiation distribution of the object is stored in the evaluation unit, depending on which the at least one scattered radiation correction factor is calculated, allows improved image quality, as the spatial distribution of the scattered radiation is taken into account.

A development, in which the object is irradiated from a plurality of projection directions and at least one scattered radiation correction factor is calculated for each projection direction, allows an improved image quality, as the dependency of the scattered radiation on the respective projection direction is taken into account. Because of the geometry of the object to be investigated, different scattered radiation correction factors are also produced for different projection directions.

A development, in which an intensity of an unattenuated primary X-ray radiation is measured as the first intensity and an intensity, which is composed of the intensity of the unattenuated primary X-ray radiation and an intensity of a secondary X-ray radiation, is measured as the second intensity, allows a high image quality.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
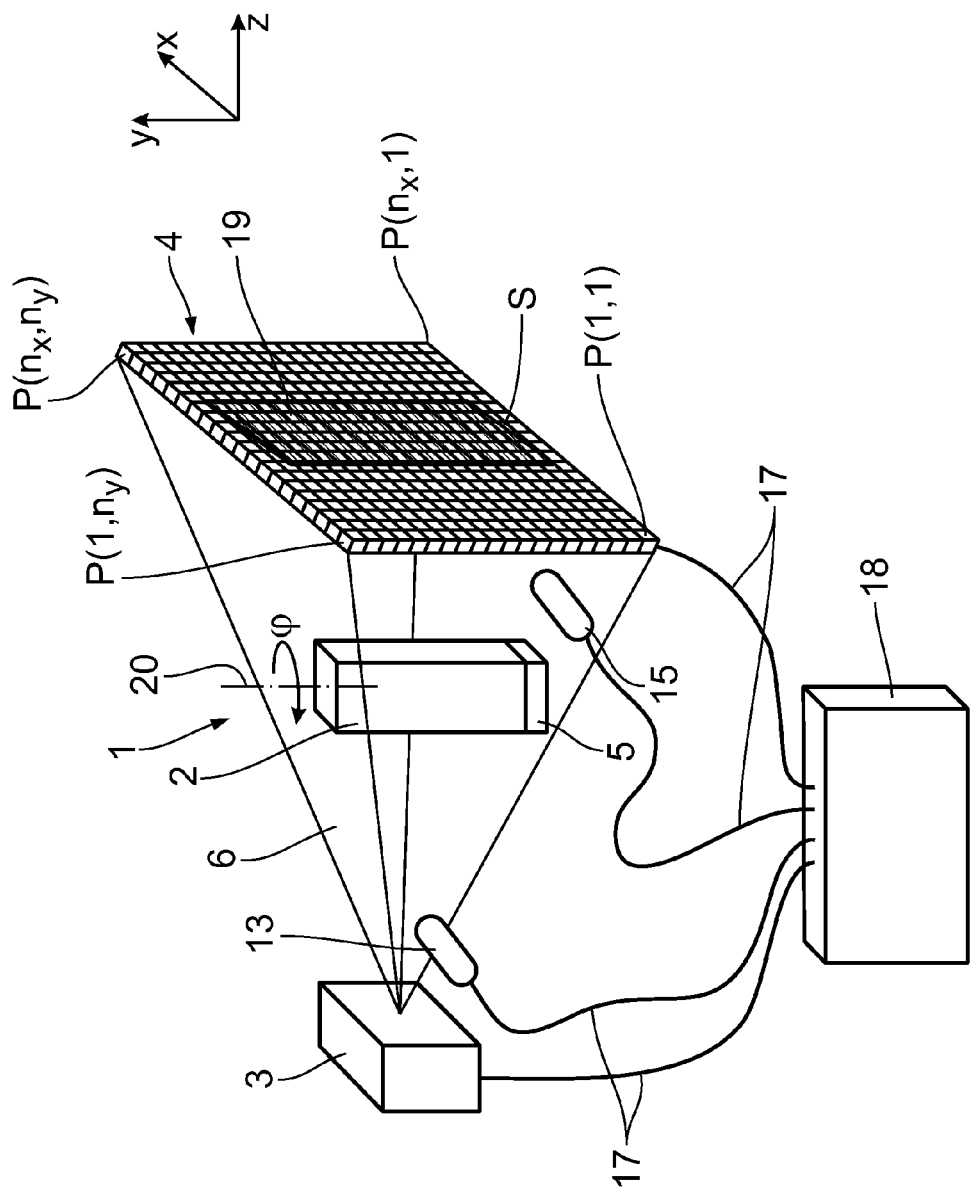
FIG. 1 is a perspective schematic view of an X-ray computer tomograph.
Figure 2:
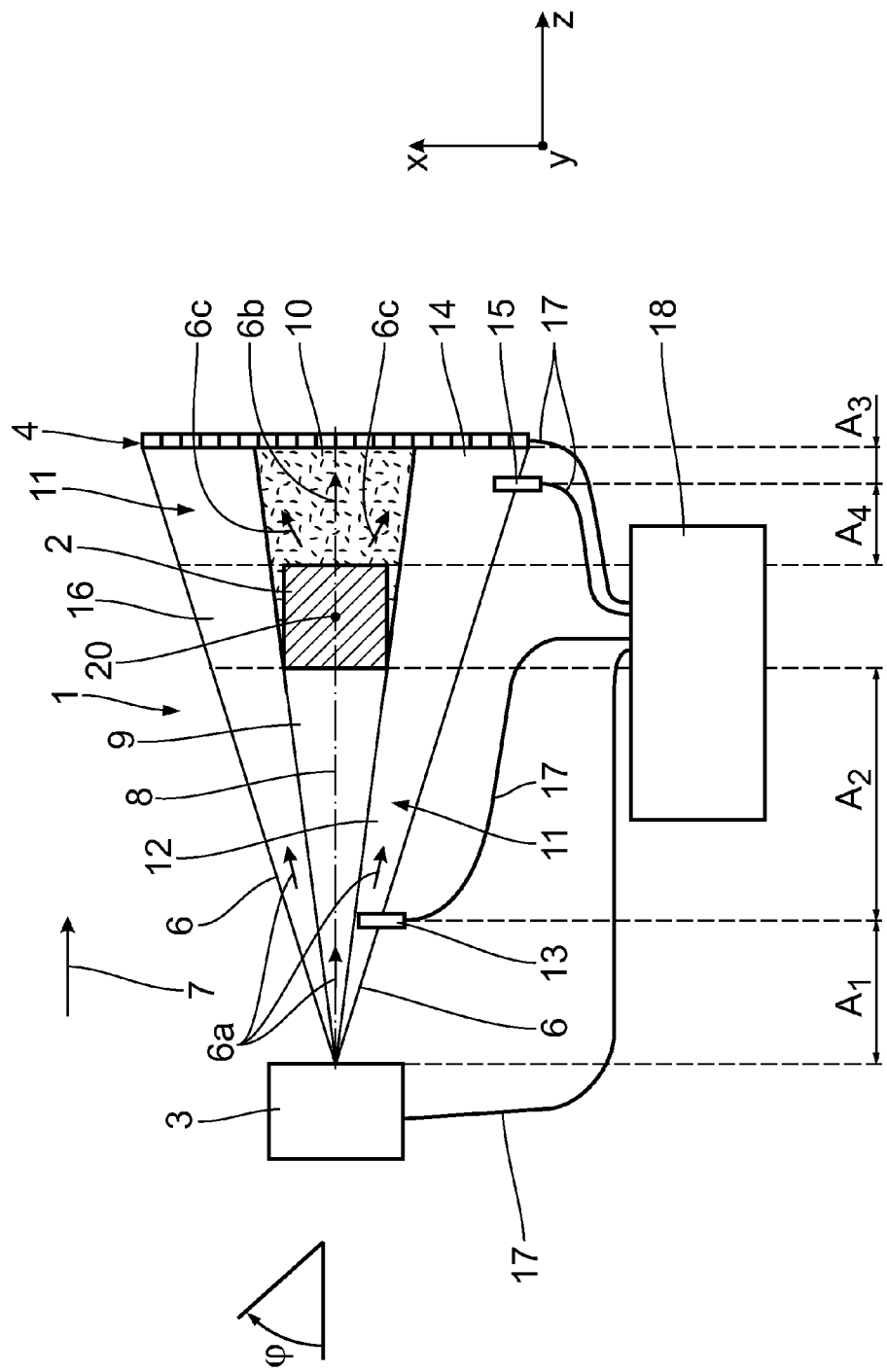
FIG. 2 is a plan view of the X-ray computer tomograph in FIG. 1.

An X-ray computer tomograph 1, to investigate an object 2, has an X-ray source 3 and an associated X-ray detector 4. Arranged between the X-ray source 3 and the X-ray detector 4 is an object carrier 5, on which the object 2 can be positioned.

The X-ray source 3 is used to produce X-ray radiation 6 being emitted conically in a beam direction 7. The beam direction 7 runs substantially parallel to a center longitudinal axis 8 of the X-ray computer tomograph 1. The X-ray source 3 is, for example, configured as an X-ray tube, the structure of which is known.

The X-ray detector 4 extends substantially in an x-y plane, which is defined by an x-direction and a y-direction extending perpendicular thereto. The center longitudinal axis 8 defines a z-direction, which runs substantially perpendicular to the x-y plane. The X-ray detector 4, in the x-and y-direction, has a large number of pixels, which are individually called P(x,y), wherein x=1 to $n_x$ and y=1 to $n_y$. The X-ray detector 4 is, for example, configured as an integrating, non-energy-dissipating flat image detector, the structure of which is known.

Depending on the geometry of the object 2 to be investigated, the X-ray radiation 6 emitted conically can be divided into different regions. In one radiation region 9, which is located between the X-ray source 3 and the object 2, primary X-ray radiation 6a impinges unattenuated on the object 2. In a projection region 10, which is located between the object 2 and the X-ray detector 4, primary X-ray radiation 6b attenuated by the object 2 impinges together with secondary X-ray radiation 6c, in other words scattered radiation, on the X-ray detector 4. The projection region 10 is also called a shadow-casting region. The radiation region 9 and the projection region 10 are surrounded by a measurement region 11, in which the unattenuated primary X-ray radiation 6a, without impinging on the object 2, arrives from the X-ray source 3 at the X-ray detector 4.

A first intensity measurement device 13 is arranged in a first measurement part region 12, which is located between the X-ray source 3 and the object 2 outside the radiation region 9. A first intensity $I_0$ of the unattenuated primary X-ray radiation 6a can be measured by means of the first intensity measurement device 13. The first intensity measurement device 13 has a first spacing $A_1$ with respect to the X-ray source 3 and a second spacing $A_2$ with respect to the object carrier 5. The spacings $A_1$, $A_2$ are in each case defined as the shortest axial distances of the first intensity measurement device 13 from the X-ray source 3 or from the object carrier 5 in the z-direction. The ratio of the first spacing $A_1$ to the second spacing $A_2$ is less than ½, in particular less than ¼, and in particular less than ⅛.

A second intensity measurement device 15 is arranged in a second measurement part region 14, which is located between the object 2 and the X-ray detector 4 outside the projection region 10. A second intensity $I_1$ of the primary X-ray radiation 6a unattenuated by the object 2 and of the secondary X-ray radiation 6c, in other words the scattered radiation, can be measured by means of the second intensity measurement device 15. The second intensity measurement device 15 has a third spacing $A_3$ from the X-ray detector 4 and a fourth spacing $A_4$ from the object carrier 5. The spacings $A_3$, $A_4$ are, in each case, defined as the shortest axial distances from the X-ray detector 4 or from the object carrier 5 in the z-direction. A ratio of the third spacing $A_3$ to the fourth spacing $A_4$ is smaller than ½, in particular smaller than ¼, and in particular smaller than ⅛. A third measurement part region 16, which is located between the first measurement part region 12 and the second measurement part region 14, is a transition region.

The intensity measurement devices 13, 15 are configured structurally the same as electronic dosimeters and supply dose outputs as measurement values, which are proportional to the intensities $I_0$, $I_1$.

The X-ray source 3, the X-ray detector 4 and the intensity measurement devices 13, 15 are connected via signal lines 17 to an evaluation unit 18. The evaluation unit 18 is configured in such a way that at least one scattered radiation correction factor F can be calculated as a function of the measured intensities $I_0$, $I_1$.

On irradiation of the object 2, a projection S of the object 2 is produced on the X-ray detector 4. Inner structures 19 of the object 2 emerge in the projection S, so a destruction-free investigation of the object 2 is possible. To produce different projections S, the object carrier 5 can be rotated about a rotational axis 20 extending parallel to the x-y-plane. The rotational position of the object carrier 5 and therefore of the object 2 is characterized by a rotation angle $\phi$. The different projections are designated S ($\phi_n$), wherein n=1 to N. The rotation angle $\phi$ is therefore a measure of the projection direction.

A first method according to the invention for investigating the object 2 by means of X-ray computer tomography will be described below.

The object 2 is arranged on the object carrier 5 and positioned at a first rotation angle $\phi_1$ relative to the X-ray source 3. The object 2 is irradiated with X-ray radiation 6a by means of the X-ray source 3. The X-ray detector 4 detects the X-ray radiation 6 impinging on it. For each pixel P(x,y), the detected X-ray radiation 6 is converted into a corresponding grey-scale value g(x,y) and transmitted to the evaluation unit 18 for evaluation.

At the same time, measurement values of the first intensity $I_0$ are measured with the first intensity measurement device 13 and measurement values of the second intensity $I_1$ are measured with the second intensity measurement device 15 and transmitted to the evaluation unit 18 for evaluation.

The first method according to the invention assumes that the secondary X-ray radiation 6c designated scattered radiation is scattered in random directions and appears as a constant and homogeneous background on the X-ray detector 4. Under this assumption the following equation applies to each pixel P(x,y):

$$g(x,y) = k \cdot [I(x,y) + I_S] = k \cdot [I_0 \cdot e^{-A(x,y)} + I_s] \quad (1)$$

Equation (1) produces a connection between the intensity I(x,y) of the attenuated primary X-ray radiation 6b, the intensity $I_0$ of the unattenuated primary X-ray radiation 6a, the intensity $I_S$ of the scattered radiation 6c and the grey-scale value g(x,y) measured by means of the X-ray detector 4 for each pixel P(x,y). k is a scaling factor between the physical intensity of the X-ray radiation 6 and the digital grey-scale values g(x,y). The scaling factor k is constant and a property of the X-ray detector 4. A(x,y) is an attenuation value for each pixel P(x,y), which describes the attenuation of the intensity $I_0$ of the unattenuated primary X-ray radiation 6a along the path from the X-ray source 3 through the object 2 to the respective pixel P(x,y) on the X-ray detector 4. The attenuation value A(x,y) is required for each pixel P(x,y) at the reconstruction of an X-ray image by means of the evaluation unit 18.

An independent, unitless superelevation factor f can be defined and determined without a conversion of the measurement values by means of the dosimetric measurements of the intensities $I_0$, $I_1$. The superelevation factor f is defined as:

$$f = \frac{I_1}{I_0} \quad (2)$$

The superelevation factor f is determined from the measurement of the intensities $I_0$, $I_1$. As the intensity $I_1$ is substantially composed of the intensity $I_0$ of the unattenuated primary X-ray radiation 6a and the intensity $I_S$ of the scattered radiation 6c, the following equation is produced:

$$f = \frac{I_1}{I_0} \approx \frac{I_0 + I_S}{I_0} = 1 + \frac{I_S}{I_0} \quad (3)$$

From equation (3) there follows for the intensity $I_S$ of the scattered radiation 6c:)

$$I_S = I_0(f-1) \quad (4)$$

If equation (4) is entered in equation (1), the intensity $I_S$ of the scattered radiation 6c can be eliminated:

$$g(x,y) = k \cdot I_0 \cdot [e^{-A(x,y)} + f - 1] \quad (5)$$

The superelevation factor f and the attenuation value A(x,y) are in each case unitless factors wherein $f \geq 1$ and $A(x,y) > 0$. The superelevation factor f describes the fraction of the scattered radiation 6c, which the X-ray detector 4 reaches. The superelevation factor f increases when the spacing between the object 2 and the X-ray detector 4 decreases.

In equation (5), the product of the scaling factor k and the intensity $I_0$ can be determined by a preliminary test without the object 2. In the preliminary test without the object 2, the superelevation factor is f=1 and the attenuation value A(x,y)=0 for all the pixels P(x,y). Equation (5) is simplified in this case into:

$$g(x,y) = k \cdot I_0 = \text{const.} \quad (6)$$

The grey-scale values g(x,y) measured in the preliminary test therefore represent the product of the scaling factor k and the intensity $I_0$.

By resolving equation (5), the attenuation value A(x,y) is produced for each pixel P(x,y) as follows:

$$A(x,y) = -\ln\left[\frac{g(x,y)}{k \cdot I_0} + 1 - f\right] \quad (7)$$

For each pixel P(x,y) equation (7) supplies a corrected attenuation value A(x,y), in which the influence of the scattered radiation 6c is substantially eliminated. By means of the attenuation values A(x,y) an X-ray image can be produced in the evaluation unit 18 by means of known reconstruction algorithms.

Under the assumption made that the scattered radiation 6c appears as a constant and homogeneous background on the X-ray detector 4, the superelevation factor f is simultaneously the scattered radiation correction factor F. Therefore:

$$F = f \quad (8)$$

Figure 3:
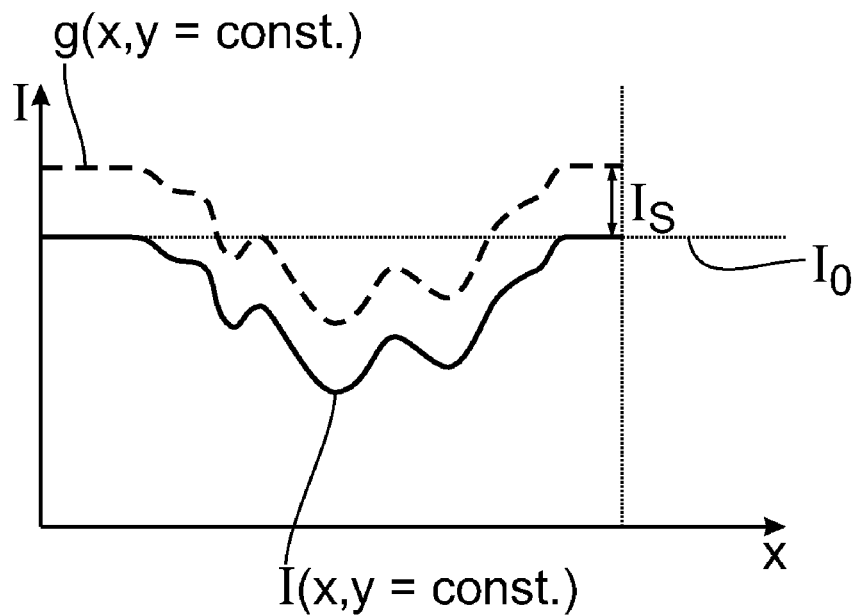
FIG. 3 is a schematic view of a scattered radiation reduction of zero order.

By means of equation (7), a scattered radiation reduction of zero order is therefore carried out. FIG. 3 illustrates the scattered radiation reduction of zero order using the example of the grey-scale values g(x,y=const.) measured in the x-direction with a constant position in the y-direction.

The dashed line in FIG. 3 shows the measured profile of the grey-scale values g(x,y=const.). The solid line is the profile of the intensity I(x,y=const.) of the attenuated primary X-ray radiation 6b after the object 2. The intensity $I_S$ of the scattered radiation 6c is a constant offset between the two lines.

The described method is repeated for N different rotation angles $\phi_n$, so different projections $S(\phi_n)$ are produced with n=1 to N. For each projection $S(\phi_n)$ a scattered radiation correction factor $F_n = f_n$, and corrected attenuation values $A_n(x,y)$ are calculated. A three-dimensional image of the object 2 can be calculated by means of the evaluation unit 18 from the corrected attenuation values $A_n(x,y)$.

In a second method according to the invention, a scattered radiation reduction of a higher order is carried out. It is assumed that the scattered radiation distribution is not homogeneous but, depending on the geometry of the object 2 to be investigated, is locally non-uniformly distributed. A relative scattered radiation distribution of a higher order can be determined by so-called Monte Carlo calculations, as a function of the geometry of the object 2 to be investigated. A relative scattered radiation distribution of this type is called a Monte Carlo scattered radiation distribution. On the assumption of a scattered radiation distribution of a higher order, the scattered radiation correction factor F(x,y) for each pixel P(x,y) produces:

$$F_n(x,y) = f_n \cdot M_n(x,y) \quad (9)$$

Figure 4:
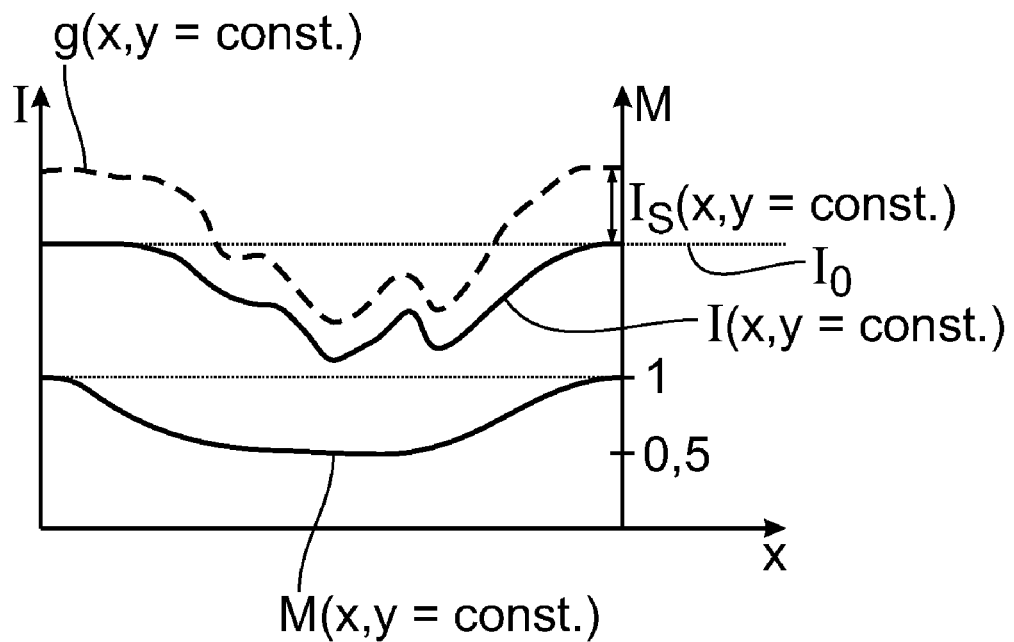
FIG. 4 is a schematic view of a scattered radiation reduction of a higher order by means of a Monte Carlo distribution.

$M_n(x,y)$ is a unitless factor between 0 and 1 and describes the relative scattered radiation distribution for a projection $S(\phi_n)$ with n=1 to N in the pixels P(x,y). FIG. 4 illustrates a scattered radiation reduction of a higher order by means of a Monte Carlo distribution M(x,y=const.). The intensity $I_S(x, y=\text{const.})$ of the scattered radiation 6c is non-uniformly distributed in the x-direction in accordance with the Monte Carlo distribution M(x,y=const.).

The X-ray computer tomograph according to the invention and the methods according to the invention for investigating an object by means of X-ray computer tomography improve the image quality, for example in the destruction-free material testing, in that an independent dosimetric estimation of the scattered radiation background is carried out. In this estimation, both a scattered radiation distribution of zero order and a scattered radiation distribution of a higher order can be taken as a starting point.

As a function of the measured first intensity of the unattenuated primary X-ray radiation 6a and the second intensity composed of the intensity of the unattenuated primary X-ray radiation 6a and the intensity of the secondary X-ray radiation 6c, a scattered radiation correction factor F is calculated, with the aid of which corrected attenuation values A(x,y) can be calculated for each pixel P(x,y), in which the influence of the scattered radiation 6c is substantially eliminated. The corrected attenuation values A(x,y) are calculated for each individual projection S corresponding to the equations (7), (8) and (9) according to the following equation:

$$A(x,y) = -\ln\left[\frac{g(x,y)}{k \cdot I_0} + 1 - F\right] \quad (10)$$

If a scattered radiation distribution of zero order is assumed, the scattered radiation correction factor F in equation (10) corresponds to the measured superelevation factor f, which is produced from the quotient of the second intensity $I_1$ and the first intensity $I_0$:

$$F = f = \frac{I_1}{I_0} \qquad (11)$$

Because of the assumption made that the scattered radiation 6c appears as a constant and homogeneous background on the X-ray detector 4, the scattered radiation correction factor F is constant for all the pixels P(x,y).

If a scattered radiation distribution of a higher order is assumed, the scattered radiation correction factor F(x,y) in equation (10) is produced as the product of the measured superelevation factor f and the assumed Monte Carlo scattered radiation distribution M(x,y):

$$F(x, y) = f \cdot M(x, y) = \frac{I_1}{I_0} \cdot M(x, y) \qquad (12)$$

The scattered radiation correction factor F(x,y), because of the assumption made, is not constant and is distributed in accordance with the Monte Carlo scattered radiation distribution M(x,y) non-uniformly over the pixels P(x,y).

By means of the corrected attenuation values A(x,y) an X-ray image with improved image quality can be produced with the aid of known reconstruction algorithms.

The scattered radiation correction factor F or the superelevation factor f are values, which enter the scattered radiation correction, with these values not having to be factors in a strictly mathematical sense.

While specific embodiments of the invention have been described in detail to illustrate the application of the principles of the invention, it will be understood that the invention may be embodied otherwise without departing from such principles.

The invention claimed is:

1. An X-ray computer tomograph for investigating an object by means of X-ray computer tomography comprising:
    an X-ray source for generating X-ray radiation;
    an X-ray detector for detecting the X-ray radiation;
    an object carrier for positioning an object to be investigated between the X-ray source and the X-ray detector; and
    an evaluation unit for evaluating the detected X-ray radiation, wherein;
    a first intensity measurement device for measuring a first intensity of the X-ray radiation is arranged between the X-ray source and the object carrier;
    a second intensity measurement device for measuring a second intensity of the X-ray radiation is arranged between the object carrier and the X-ray detector outside a projection region of the object;
    the intensity measurement devices are connected to the evaluation unit to transmit the measured intensities; and
    the evaluation unit is configured in such a way that at least one scattered radiation correction factor is calculable depending on the measured intensities.

2. An X-ray computer tomograph according to claim 1, wherein a first spacing defined as the shortest axial distance of the first intensity measurement device from the X-ray source in relation to a second spacing defined as the shortest axial distance of the first intensity measurement device from the object carrier is smaller than ½.

3. An X-ray computer tomograph according to claim 1, wherein the first intensity measurement device is arranged outside an irradiation region of the object.

4. An X-ray computer tomograph according to claim 1, wherein a third spacing defined as the shortest axial distance of the second intensity device from the X-ray detector in relation to a fourth spacing defined as the shortest axial distance of the second intensity measurement device from the object carrier is smaller than ½.

5. An X-ray computer tomograph according to claim 1, wherein the intensity measurement devices are configured as electronic dosimeters.

6. An X-ray computer tomograph according to claim 1, wherein the intensity measurement devices are constructed identically.

7. An X-ray computer tomograph according to claim 1, wherein the first intensity measurement device is arranged in such a way that an intensity of an unattenuated primary X-ray radiation is measurable as the first intensity and the second intensity measurement device is arranged in such a way that an intensity, which is composed of the intensity of the unattenuated primary X-ray radiation and an intensity of a secondary X-ray radiation, is measurable as the second intensity.

8. An X-ray computer tomograph according to claim 1, wherein the intensity measurement devices are arranged in a measurement region, in which a primary unattenuated X-ray radiation arrives from the X-ray source at the X-ray detector, without impinging on the object to be investigated.

9. An X-ray computer tomograph according to claim 1, wherein the evaluation unit is configured in such a way that, for each pixel P(x,y) of the X-ray detector, a corrected attenuation value is calculable according to the equation $$A(x, y) = -\ln\left[\frac{g(x, y)}{k \cdot I_0} + 1 - F\right]$$

wherein
    A(x,y) is the corrected attenuation value for the pixel P(x, y),
    g(x,y) is a measured grey-scale value for the pixel P(x,y),
    $k \cdot I_0$ is a constant which is determinable in preliminary tests and
    F is the scattered radiation correction factor.

10. An X-ray computer tomograph according to claim 1, wherein a first spacing defined as the shortest axial distance of the first intensity measurement device from the X-ray source in relation to a second spacing defined as the shortest axial distance of the first intensity measurement device from the object carrier is smaller than ¼.

11. An X-ray computer tomograph according to claim 1, wherein a first spacing defined as the shortest axial distance of the first intensity measurement device from the X-ray source in relation to a second spacing defined as the shortest axial distance of the first intensity measurement device from the object carrier is smaller than ⅛.

12. An X-ray computer tomograph according to claim 1, wherein a third spacing defined as the shortest axial distance of the second intensity device from the X-ray detector in relation to a fourth spacing defined as the shortest axial distance of the second intensity measurement device from the object carrier is smaller than ¼.

13. An X-ray computer tomograph according to claim 1, wherein a third spacing defined as the shortest axial distance of the second intensity device from the X-ray detector in relation to a fourth spacing defined as the shortest axial distance of the second intensity measurement device from the object carrier is smaller than 1/8.

14. A method for investigating an object by means of X-ray computer tomography, the method comprising the steps:
- positioning an object to be investigated between an X-ray source and an X-ray detector;
- irradiating the object with X-ray radiation;
- detecting the X-ray radiation; and
- evaluating the detected X-ray radiation by means of an evaluation unit, wherein:
- during the irradiation of the object, a first intensity of the X-ray radiation between the X-ray source and the object is measured;
- during the irradiation of the object, a second intensity of the X-ray radiation between the object and the X-ray detector outside a projection region of the object is measured; and
- during the evaluation, at least one scattered radiation correction factor is calculated depending on the measured intensities and the detected X-ray radiation is corrected with the at least one scattered radiation correction factor.

15. A method according to claim 14, wherein the intensities are measured at the same time.

16. A method according to claim 14, wherein the first intensity is measured outside an irradiation region of the object.

17. A method according to claim 14, wherein at least one Monte Carlo scattered radiation distribution of the object is stored in the evaluation unit, depending on which the at least one scattered radiation correction factor is calculated.

18. A method according to claim 14, wherein the object is irradiated from a plurality of projection directions and at least one scattered radiation correction factor is calculated for each projection direction.

19. A method according to claim 14, wherein an intensity of an unattenuated primary X-ray radiation is measured as the first intensity and an intensity, which is composed of the intensity of the unattenuated primary X-ray radiation and an intensity of a secondary X-ray radiation, is measured as the second intensity.

* * * * *